US006781370B1

(12) United States Patent
Hinken et al.

(10) Patent No.: US 6,781,370 B1
(45) Date of Patent: Aug. 24, 2004

(54) TESTING DEVICE FOR DETECTING AND DETERMINING MATERIAL INHOMOGENEITIES

(76) Inventors: Johann H. Hinken, Innerste Au 34, D-31139 Hildesheim (DE); Yury Tavrin, Carl-Justi-Str. 24, D-52121 Bonn (DE)

(*) Notice: Subject to any disclaimer, the term of this patent is extended or adjusted under 35 U.S.C. 154(b) by 0 days.

(21) Appl. No.: 09/806,739
(22) PCT Filed: Oct. 5, 1999
(86) PCT No.: PCT/EP99/07440
§ 371 (c)(1),
(2), (4) Date: Feb. 1, 2002
(87) PCT Pub. No.: WO00/20856
PCT Pub. Date: Apr. 13, 2000

(30) Foreign Application Priority Data

Oct. 6, 1998 (DE) .......................................... 198 46 025

(51) Int. Cl.[7] .............................................. G01N 27/72
(52) U.S. Cl. ........................ 324/242; 324/224; 324/243
(58) Field of Search ................................. 324/242, 243, 324/237, 238, 239, 240, 241, 248, 224

(56) References Cited

U.S. PATENT DOCUMENTS

| 4,534,405 A | | 8/1985 | Hulek et al. | |
|---|---|---|---|---|
| 4,950,990 A | * | 8/1990 | Moulder et al. | ............ 324/224 |
| 5,331,278 A | * | 7/1994 | Evanson et al. | ............ 324/240 |
| 5,430,376 A | | 7/1995 | Viertl | |
| 5,537,037 A | | 7/1996 | Otaka et al. | |
| 6,025,713 A | * | 2/2000 | Morooka et al. | ............ 324/248 |

FOREIGN PATENT DOCUMENTS

| DE | 1 59 276 A | 3/1983 |
|---|---|---|
| DE | 40 03 060 A1 | 8/1991 |
| DE | 40 32 092 A1 | 4/1992 |
| EP | 0 135 204 A2 | 3/1985 |

OTHER PUBLICATIONS

Kaidanov et al., "Investigation of Galvano– and Thermamagnetic Phenomena in Semiconductors by a Transient Method," *Industrial Laboratory*, 32(9), 1343–1346 (Sep. 1966).

Nave et al., "Micromagnetic Susceptometer," *Rev. Sci. Instrum.*, 51 (5), 591–596 (May 1980).

* cited by examiner

Primary Examiner—Jay Patidar
(74) Attorney, Agent, or Firm—Leydig, Voit & Mayer Ltd

(57) ABSTRACT

The present invention relates to a testing device for detecting and determining material inhomogeneities in electrically conductive samples (10), comprising a support (30) for the samples (10) to be tested, a temperature regulating device (30, 50, 60) for configuring a temperature profile in the sample (10), a drive connected to the support (30) for changing the position of the sample (10) and at least one measuring sensor (20) for contactless measurement of the magnetic field outside the sample (10).

18 Claims, 2 Drawing Sheets

TESTING DEVICE FOR DETECTING AND DETERMINING MATERIAL INHOMOGENEITIES

BACKGROUND OF THE INVENTION

The invention relates to a testing device for detecting and localizing material inhomogeneities in electrically conductive subjects or samples.

According to the state of the art, with the testing of electromagnetic inclusions the subject is premagnetized and subsequently scanned with a magnetic field measuring apparatus as published by J. Tavrin and by J. Hinken at the "7. Europäischen Konferenz für zerstörungsfreies Testen" (7th European Conference for non-destructive testing) in Copenhagen 1998 and in the document of the Institute Dr. Forster 04/95. By way of the scanning in at least two planes one may infer the depth position of the inclusions. With the testing for non-ferromagnetic inclusions or inhomogeneities the subject is brought into an external magnetic field, wherein this may also be the naturally present earth's field. On account of the susceptibility fluctuations in the subject the magnetic field outside the subject is location-dependent. With measurement with a magnetometer one may draw conclusions on the non-ferromagnetic inhomogeneities, as is known from the publication by J. P. Wikswo in IEEE Trans. Appl. Supercond., Volume 3, No. 1 of March 1993. Both measuring methods do not use a directed temperature change of the subject.

Thermoelectric effects were up to now only used for the sorting of similar materials, not for the detection and localization of inhomogeneities, as is known from a publication by McMaster in "Non-destructive Testing Handbook", Second Edition, Volume 4, Electromagnetic Testing of the American Society for Non-destructive Testing of 1996 and from a publication by A. S. Karolik and A. A. Lukhvich in Sov. J. Nondestruct. Test., Volume 26, No. 10 of October 1990. Furthermore for this an electrical and mechanical contacting of the component is necessary.

The apparatus for magnetic field measurement described according to the state of the art, i.e. based on the remanence and the susceptibility have the disadvantage that the measuring signals are not strong enough to ascertain and to quantify also small inhomogeneities lying far below the surface. Measuring apparatus with thermoelectric effects have not yet been used for the detection and localization of inhomogeneities.

BRIEF SUMMARY OF THE INVENTION

It is the object of the invention, with magnetic field-supported, non-destructive testing of electrically conductive subjects to intensify the magnetic field signals and thus to increase the measuring resolution. This applies to inhomogeneities close to the surface as well as to those which lie deep below the surface.

On account of the temperature profile set in a sample by way of the temperature setting means, the magnetic field signals of the material of the probe, in particular the segregations, are increased in a manner such that material inhomogeneities may be detected and localized when the magnetic field outside the sample is measured during a position change. By way of this, material inhomogeneities on the surface and also deep below the surface of the sample may be detected in a non-destructive and exact manner.

The testing device according to the invention measures and tests in a non-destructive manner, wherein the device sets the temperature or the temperature gradient in the measured object in a targeted manner and measures the magnetic field outside the measured object. Characteristic magnetic field signatures arise on account of various physical effects. To these there belong temperature dependency of the susceptibility, thermoelectric effects and thermomagnetic effects.

Measuring signals which are based on susceptibility differences become stronger when this difference is greater. Now the susceptibility of many materials becomes larger with a reducing temperature. It is often roughly proportional to the inverse value of the absolute temperature. A cooling of the subject therefore increases the susceptibility of the base material and the inclusion and thus also the difference of both, as is known from the publication by W. Schultz "Dielektrische und magnetische Eigenschaften der Werkstoffe" (Dielectric and magnetic properties of the materials), Vieweg, Braunschweig of 1970. With this the cooling is contrast-intensifying. This method based on the susceptibility difference permits the detection also of inhomogeneities lying deep below the surface.

Of the thermoeletric effects in this context amongst others the Seebeck effect and the first Benedicks effect are used, which are known from the publication by Joachim Schubert: "Physikalische Effect" (Physical effects), Physik publishing house, Weinheim 1984.

If two contact locations lie between two different materials at different temperatures, between them there arises an electrical voltage. This is the thermoelectric voltage, the effect is the Seebeck effect. In the component to be tested these contact locations are formed by the border layer between the base material and the inclusion. If a temperature gradient lies over the inclusion there is created the condition for the existance of thermoelectric voltages and thermoelectric currents. These currents in turn also outside the tested object produce a magnetic field which may be detected with a magnetic field measuring apparatus. The mentioned temperature gradient may be created by cooling or heating. The polarity of the produced magnetic field together with the polarity of the temperature gradient give indications as to the material class of the inclusions. The inclusions to be detected with this must be electrically conductive.

Fractures or insulating inclusions in otherwise homogeneous material may be detected by way of the first Benedicks effect. According to the Benedicks effect in a homogeneous conductor there arises a thermoeletric voltage when there is present a high temperature slope. This thermoeletric voltage in turn results in thermoelectric currents whose distribution is disturbed by fractures and insulating inclusions. Corresponding changes in the magnetic field which are produced outside the tested object by way of these currents may be detected.

According to the invention the thermoeletric effects are observed without creating an electrical and mechanical contact. This has the advantages that the errors by way of unreproducable contacts are avoided, that the components may be scanned with more degrees of freedom and that with this there are left no traces of scratches. This measuring method based on thermoelectric effects permits inhomogeneities lying deep below the surface to be detected.

Further advantageous embodiments of the invention are the subject-matter of the dependent claims.

With the use of the thermoelectric effects the temperature slope in subsequent measurements may be differently set in a targeted manner. The measuring signals resulting therefrom give further information on the examined inhomogeneity, as e.g. an improved localization and shape detection.

BRIEF DESCRIPTION OF THE DRAWINGS

Further details, features and advantages of the invention result from the subsequent desription of one advantageous embodiment form of the invention by way of the drawings.

There are shown in

DETAILED DESCRIPTION OF THE INVENTION

Figure 1:
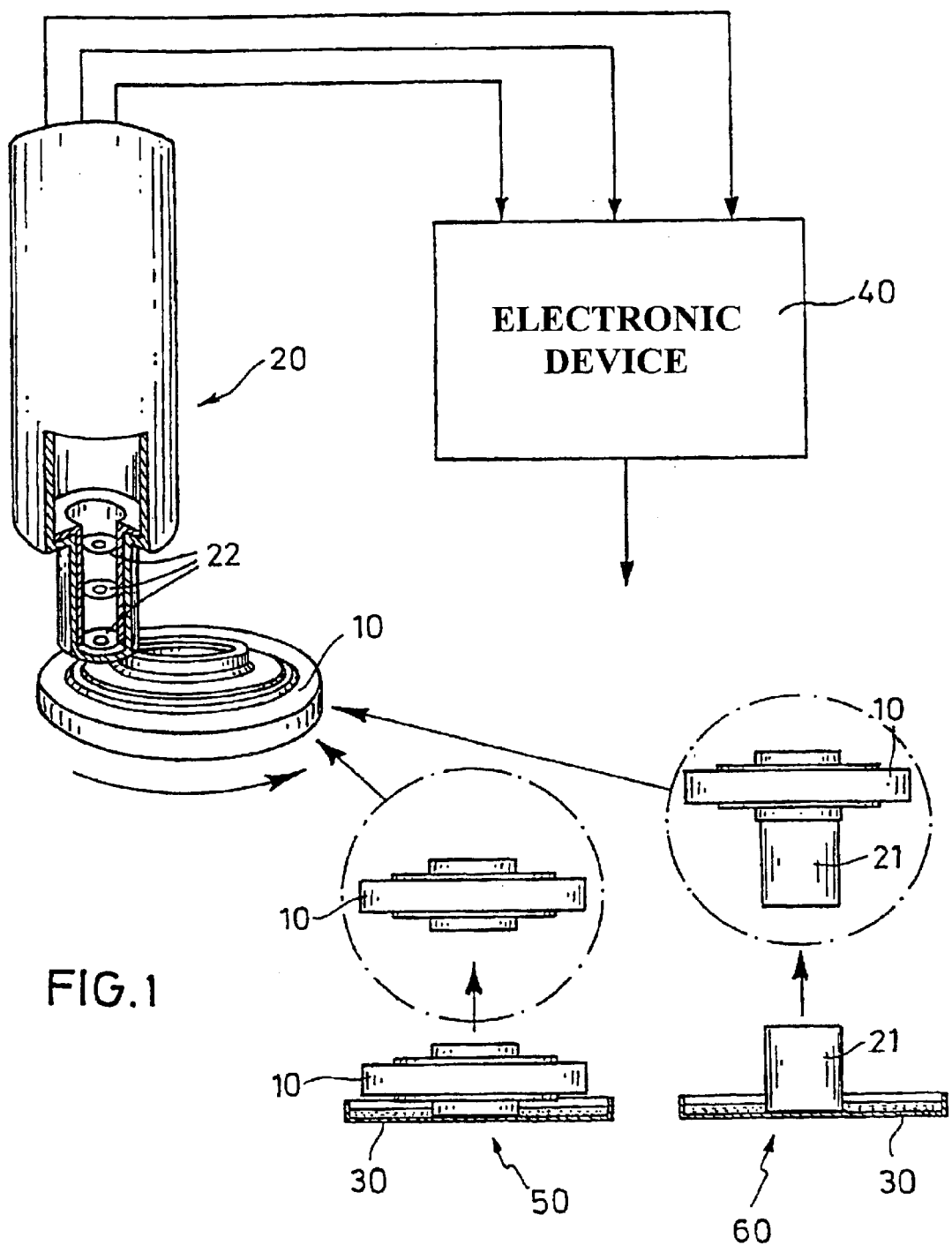
FIG. 1 a schematic representation of a testing device according to the invention.

In FIG. 1 there is shown an advantageous embodiment example of a testing device for detecting and localizing material inhomogeneities in a measured object or a sample 10, which in particular is pre-magnetized. The sample 10 is a circular disk which is carried by a short tube piece 21 which serves as a distancer and a cold bridge. The lower side of the tube 21 is cooled with cooling fluid, in particular liquid nitrogen. In the sample 10 itself thus there arises a temperature gradient, i.e. a temperature slope with which at the top there is present a higher temperature and at the bottom a lower temperature. The sample 10 is rotated and at its upper side the magnetic field is scanned with a magnetic field measuring apparatus or a gradiometer 20. As a magnetic field measuring apparatus there is used a Squid gradiometer 20 of the second order (HMT), as shown in FIG. 1, which measures the normal component of the magnetic field on the surface of the subject or of the sample 10. This magnetic field measuring apparatus 20 consists of three individual Squid sensors 22 which are manufactured of high-temperature superconductors. For operation they are filled with liquid nitrogen. The three sensors 22 and their electronic channels are mechanically and electronically matched such that the background fields are extremely supressed. Only signals from the neighboring sample 10 are indicated, and specifically with a particularly high sensitivity. This measuring system thus does not require any magnetic shielding around the sample 10 and the sensors 22, as is otherwise often necessary with Squid measuring systems.

There are various cooling methods, as shown in FIG. 1, which are based on the use of a cooling fluid. With the use of a first method 50 the probe 10 is cooled over a large surface on the lower side, and there sets in a certain temperature slope in the sample 10. According to a second method 60 a tube piece 21 is cooled whose diameter may be suitably selected and varied. With the variation of the temperature slope, inhomogeneities present may be localized. The sample 10 may be measured from both sides by turning round. With this, mostly a polarity change and an amplitude change are expected. The gradiometer 20 or the cryostat with gradiometer, in particular with "epoxy dewar" or epoxy-pole has a height of approx. 800 mm, wherein the diameter of the lower part is approx. 90 mm. The gradiometer 20 may be varied in its height above the sample 10 in order in subsequent measurements to determine the depth of an inhomogeneity.

The three Squid sensors 22 are normally as described above, connected to a gradiometer 20 of the second order. In FIG. 1 three Squid sensors 22 are connected to an electronic device 40, wherein the electronic device 40 indicates a measuring result in $((d^2Bz)//dz^2))(t)$ as is indicated by the arrow leading away from the electronic device 40. This connecting may be simply changed so that the lower two and also the upper two Squid sensors 22 may in each case be connected to gradiometers of the first order. In this manner it is possible with these two magnetic field measuring apparatus to simultaneously measure at different distances to the sample 10 and furthermore to carry out a depth detection of inhomogeneities present.

Figure 3:
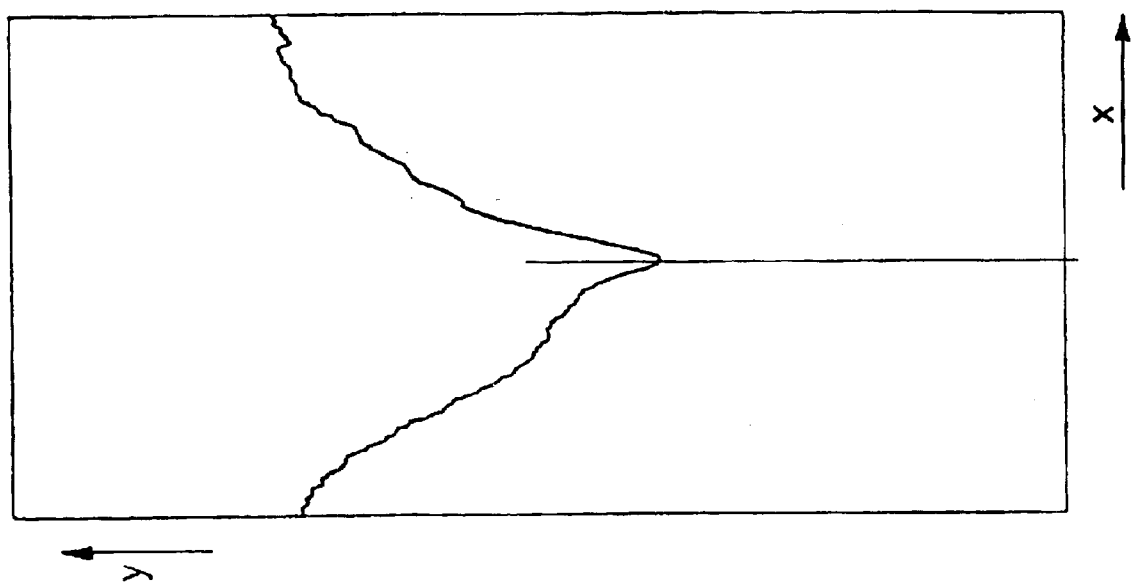
FIG. 3 a graphic representation of a measuring signal of a sample which has been determined by the testing device of FIG. 1.
Figure 2:
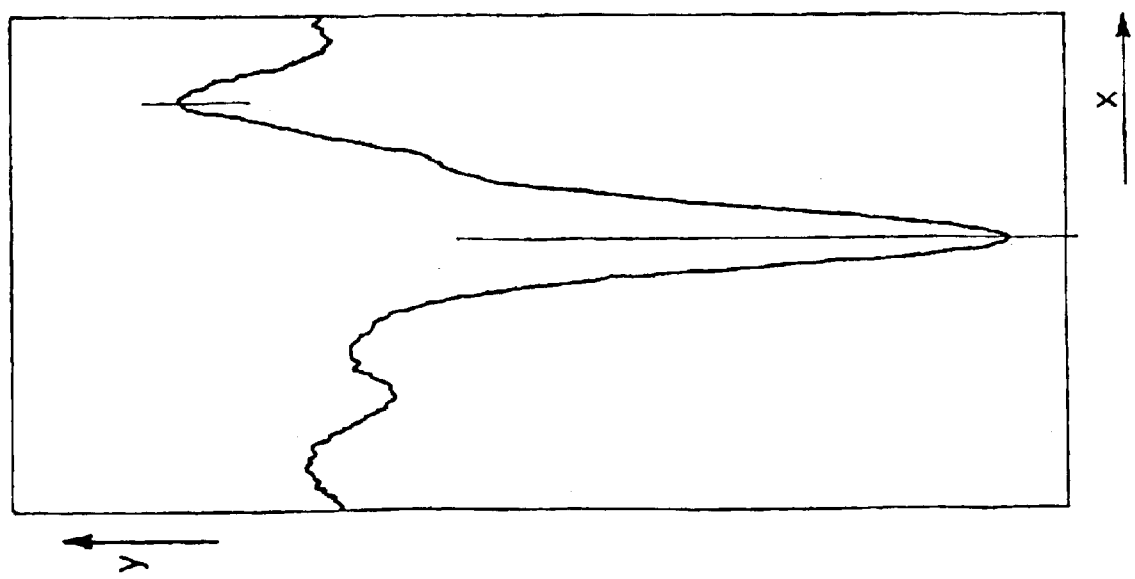
FIG. 2 a graphic representation of a measuring signal of a sample, which has been determined by the testing device of FIG. 1.

The FIGS. 2 and 3 show graphic representations of measuring signals which were recorded with a testing device of FIG. 1, wherein the disk consisted of a nickel base alloy Waspaloy with a disk diameter of approx. 180 mm and a disk thickness of approx. 40 mm. In the FIGS. 2 and 3 the x-axis indicates the rotational angle of the sample 10 between 0° and 360°, wherein the y-axis indicates the magnetic field strength in $(d^2Bz)//dz^2)$. On the surface, by way of segregation sets at an angle φ which represents the minimum of the graphs, a hard-α segregation was recognized and localized.

FIG. 2 shows a distinct measuring signal at the location of the segregation, created by currents which according to the Seebeck effect flow in the sample. In FIG. 2 the temperature which means the measuring signal is very distinctive.

Under conditions which are otherwise the same, FIG. 3 shows the measurement with a weekly set temperature gradient with a correspondingly less strong measuring signal with the minimum of the graphs at φ=190°.

What is claimed is:

1. A testing device for detecting and localizing material inhomogeneities in electrically conductive samples comprising a holder for the sample to be tested, a temperature setting device for forming a temperature profile in the sample, and at least one measuring sensor for the contactless measurement of the magnetic field outside the sample, wherein several measuring sensors are provided at a different distance to the sample.

2. The testing device of claim 1, wherein the holder is connected to a rotational drive for rotating the sample.

3. The testing device of claim 2, wherein the measuring sensors comprise a Squid sensor.

4. The testing device of claim 3, wherein the Squid sensor is a Squid magnetometer.

5. The testing device of claim 3, wherein Squid sensor comprises a Squid gradiometer.

6. The testing device of claim 1, wherein the measuring sensors comprise a Squid sensor.

7. The testing device of claim 6, wherein the Squid sensor is a Squid magnetometer.

8. The testing device of claim 6, wherein Squid sensor comprises a Squid gradiometer.

9. A method for detecting and localizing material inhomogeneities in electrically conductive samples, which method comprises (a) bringing a sample to a predetermined temperature profile, (b) contactlessly measuring the magnetic field outside the sample using several measuring sensors which are provided at a different distance to the sample, wherein the measuring resolution is increased, and whereupon material inhomogeneities are detected and localized.

10. The method of claim 9, wherein the sample is rotated.

11. The method of claim 10, wherein from the polarity of the measuring signal and the direction of the temperature gradient one may infer the type of homogeneity.

12. The method of claim 11, wherein for the improved localization and shape determination of the inhomogeneity the temperature profile in the sample is differently set in subsequent measurements.

13. The method of claim 10, wherein for the improved localization and shape determination of the inhomogeneity the temperature profile in the sample is differently set in subsequent measurements.

14. The method of claim 9, wherein from the polarity of the measuring signal and the direction of the temperature gradient one may infer the type of homogeneity.

15. The method of claim 14, wherein for the improved localization and shape determination of the inhomogeneity the temperature profile in the sample is differently set in subsequent measurements.

16. The method of claim 9, wherein for the improved localization and shape determination of the inhomogeneity the temperature profile in the sample is differently set in subsequent measurements.

17. The method of claim 9, wherein, in subsequent measurements, the magnetic field is measured at different distances to the sample.

18. The method of claim 9, wherein one simultaneously measures with several measuring sensors.

* * * * *